United States Patent
Saha

(10) Patent No.: US 10,806,767 B1
(45) Date of Patent: Oct. 20, 2020

(54) METHOD AND PREPARATION FOR THE DELIVERY OF SELECTIVE SMALL MOLECULE PHYTOCHEMICAL BASED AND PHARMACOLOGICALLY ACTIVE MEDIA THROUGH A CELL MEMBRANE TO ENHANCE FOOD GROUPS FOR HEALTH PROTECTION AND BENEFITS

(71) Applicant: Anuj K Saha, Martinez, GA (US)

(72) Inventor: Anuj K Saha, Martinez, GA (US)

( * ) Notice: Subject to any disclaimer, the term of this patent is extended or adjusted under 35 U.S.C. 154(b) by 0 days.

(21) Appl. No.: 16/351,005

(22) Filed: Mar. 12, 2019

(51) Int. Cl.
| | | |
|---|---|---|
| *A61K 36/00* | (2006.01) | |
| *A61K 36/9066* | (2006.01) | |
| *A23L 5/20* | (2016.01) | |
| *A61K 31/035* | (2006.01) | |
| *A23L 33/175* | (2016.01) | |
| *A61K 47/18* | (2017.01) | |
| *A23L 33/105* | (2016.01) | |

(52) U.S. Cl.
CPC ............ *A61K 36/9066* (2013.01); *A23L 5/23* (2016.08); *A23L 33/105* (2016.08); *A23L 33/175* (2016.08); *A61K 31/035* (2013.01); *A61K 47/183* (2013.01)

(58) Field of Classification Search
None
See application file for complete search history.

(56) References Cited

FOREIGN PATENT DOCUMENTS

JP      2016028018 A * 2/2016

OTHER PUBLICATIONS

Singh et al, Isonnalto-oligosaccharides, lycopene and their combination (co-biotic) ameliorated high Fat diet-induced Gut derangements, metabolic endotoxemia, adiposity and Non-alcoholic fatty liver in mice. Obesity Reviews, (Apr. 2016) vol. 17, Supp. Suppl. 2, pp. 163. (Year: 2016).*

Jiang et al, Structure and antioxidant activity of Maillard reaction products from .alpha.-lactalbumin and .beta.-lactoglobulin with ribose in an aqueous model system. Food Chemistry (2012), vol. 133, No. 3, pp. 960-968 (Year: 2012).*
Liu et al, Recent advances in flavonoid-grafted polysaccharides: Synthesis, structural characterization, bioactivities and potential applications: International journal of biological macromolecules, (Sep. 2018) vol. 116, pp. 1011-1025 (Year: 2018).*
[Website] Publisher: SuperBio [Accessed on Dec. 14, 2019] Retrieved From: https://www.superbioprobiotic.com/blog/BOSVIEW/CoBiotics-next-generation-probiotics/.
[Website] Publisher: Lapidot Medical [Accessed on Dec. 14, 2019] Retrieved From: http://www.lapidotmedical.com/products.php?id=1060.
[Website] Publisher National Institutes of Health [Accessed on Dec. 14, 2019] Retrieved From: https://www.nia.nih.gov/health/dietary-supplements#what.
[Website] Publisher National Institutes of Health [Accessed on Dec. 14, 2019] Retrieved From: https://ods.od.nih.gov/HealthInformation/dictionary.aspx.
[Website] Publisher National Institutes of Health—US National Library of Medicine [Accessed on Dec. 14, 2019] Retrieved From: https://www.ncbi.nlm.nih.gov/pubmed/29876980.
[Website] Amazon [Accessed on Dec. 14, 2019] Retrieved From: https://www.amazon.com/s?k=lycopene&ref=nb_sb_noss_1.
[Website] Amazon [Accessed on Dec. 14, 2019] Retrieved From: https://www.amazon.com/s?k=isomaltooligosaccharide&crid=1JENNORNVOBJ&sprefix=isomalto%2Caps%2C168&ref=nb_sb_ss_i_1_8.

* cited by examiner

*Primary Examiner* — Qiuwen Mi
(74) *Attorney, Agent, or Firm* — RB Consulting Inc.; James Carson

(57) ABSTRACT

The method and preparation for the delivery of selective small molecule phytochemical based and pharmacologically active media through a cell membrane to enhance food groups for health protection and benefits is a method of selectively delivering a pharmacologically active small molecule phytochemical to specifically targeted cells within a body. The method comprises attaching the pharmacologically active small molecule phytochemical to a nutrient. The nutrient is selected such that the nutrient is selectively brought into the targeted cells as part of the metabolic process. The selected nutrient brings the pharmacologically active small molecule phytochemical through a cell membrane with the selected nutrient. The methodologies/process described in this application are referred to as the "Guru-Vishnu" process.

1 Claim, 18 Drawing Sheets

Scenario 4

Scenario 7

METHOD AND PREPARATION FOR THE DELIVERY OF SELECTIVE SMALL MOLECULE PHYTOCHEMICAL BASED AND PHARMACOLOGICALLY ACTIVE MEDIA THROUGH A CELL MEMBRANE TO ENHANCE FOOD GROUPS FOR HEALTH PROTECTION AND BENEFITS

CROSS-REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

Field of the Invention

The present invention relates to the field of microstructural technology, more specifically, an artificial structure configured to deliver a phytochemical based pharmacologically active media through a cell membrane. (B82Y5/00)

SUMMARY OF INVENTION

The method and preparation for the delivery of selective small molecule phytochemical based and pharmacologically active media through a cell membrane to enhance food groups for health protection and benefits is a process that is configured for use in delivering a selective small molecule phytochemical based and pharmacologically active media (hereinafter selective small molecule P and P active media) through a cell membrane. The selective small molecule P and P active media is a chemical substance that has a biochemical or physiological effect on a biological organism. By small molecule is meant that the pharmacologically active media has a molecular weight of less than 1000 Daltons. The method and preparation for the delivery of selective small molecule phytochemical based and pharmacologically active media through the cell membrane to enhance food groups for health protection and benefits delivers the selective small molecule P and P active media through the cell membrane. The method and preparation for the delivery of selective small molecule phytochemical based and pharmacologically active media through a cell membrane to enhance food groups for health protection and benefits delivers the selective small molecule P and P active media through the cell membrane by taking advantage of the metabolic activity of the cell. Specifically, the selective small molecule P and P active media attaches to a foodstuff that is brought through the cell membrane as part of the cell's normal metabolic activity.

The applicants demonstrate the viability of the above approach by disclosing the following methods and preparations for the delivery of selective small molecule P and P active media through a cell membrane.

These together with additional objects, features and advantages of method and preparation for the delivery of selective small molecule phytochemical based and pharmacologically active media through a cell membrane to enhance food groups for health protection and benefits will be readily apparent to those of ordinary skill in the art upon reading the following detailed description of the presently preferred, but nonetheless illustrative, embodiments when taken in conjunction with the accompanying drawings.

In this respect, before explaining the current embodiments of method and preparation for the delivery of selective small molecule phytochemical based and pharmacologically active media through a cell membrane to enhance food groups for health protection and benefits in detail, it is to be understood that method and preparation for the delivery of selective small molecule phytochemical based and pharmacologically active media through a cell membrane to enhance food groups for health protection and benefits is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of method and preparation for the delivery of selective small molecule phytochemical based and pharmacologically active media through a cell membrane to enhance food groups for health protection and benefits.

It is therefore important that the claims be regarded as including such equivalent construction insofar as they do not depart from the spirit and scope of method and preparation for the delivery of selective small molecule phytochemical based and pharmacologically active media through a cell membrane to enhance food groups for health protection and benefits. It is also to be understood that the phraseology and terminology employed herein are for purposes of description and should not be regarded as limiting.

DETAILED DESCRIPTION OF THE EMBODIMENT

Figure 1:
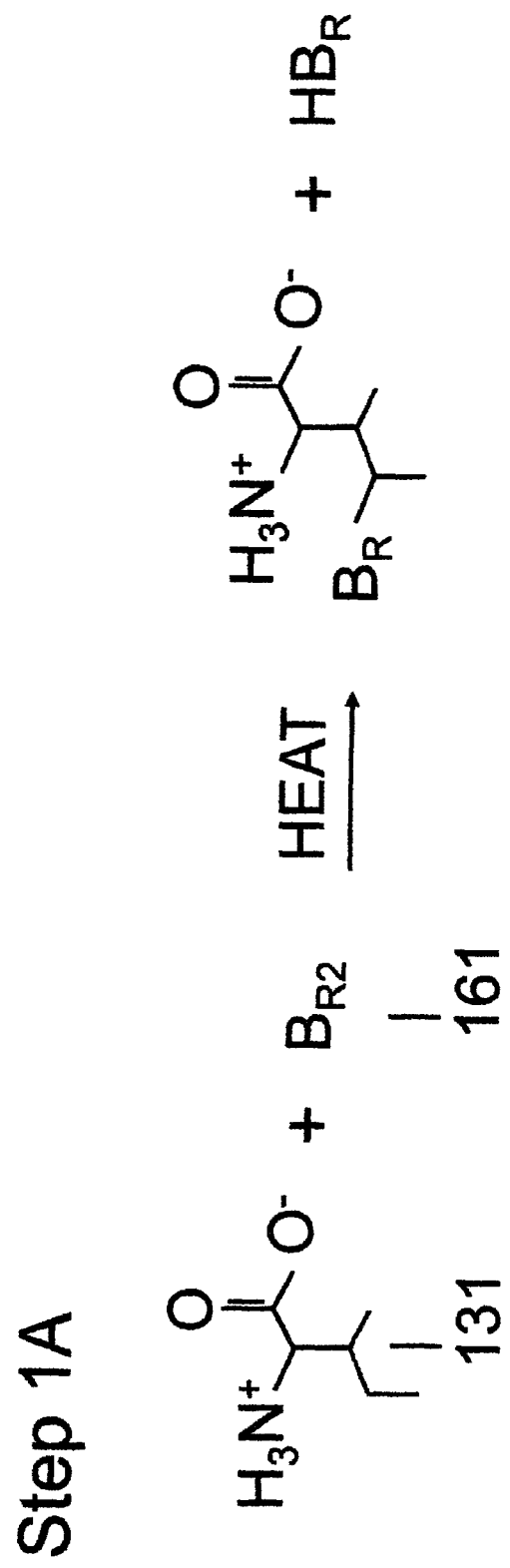
FIG. 1 is a detail view of an embodiment of the disclosure.
Figure 2:
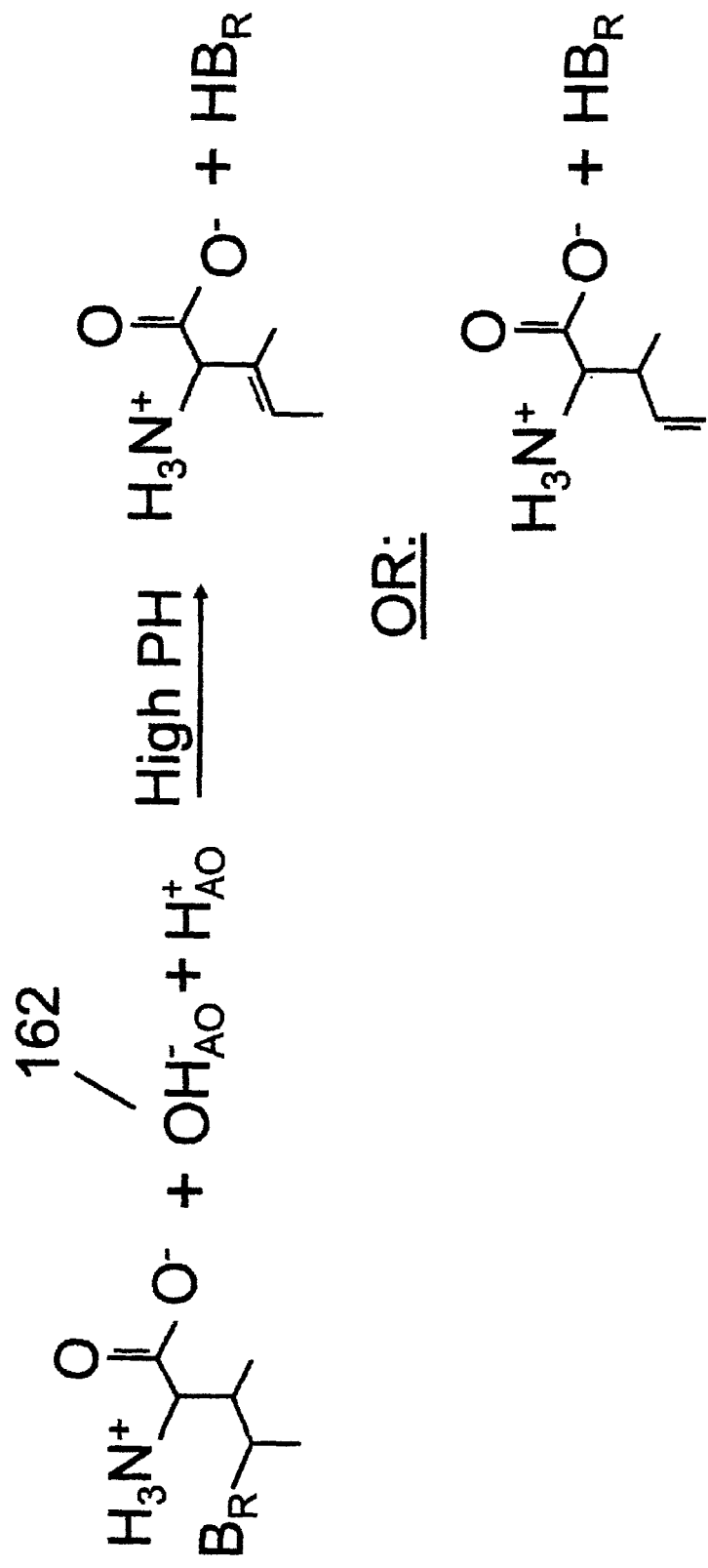
FIG. 2 is a detail view of an embodiment of the disclosure.
Figure 3:
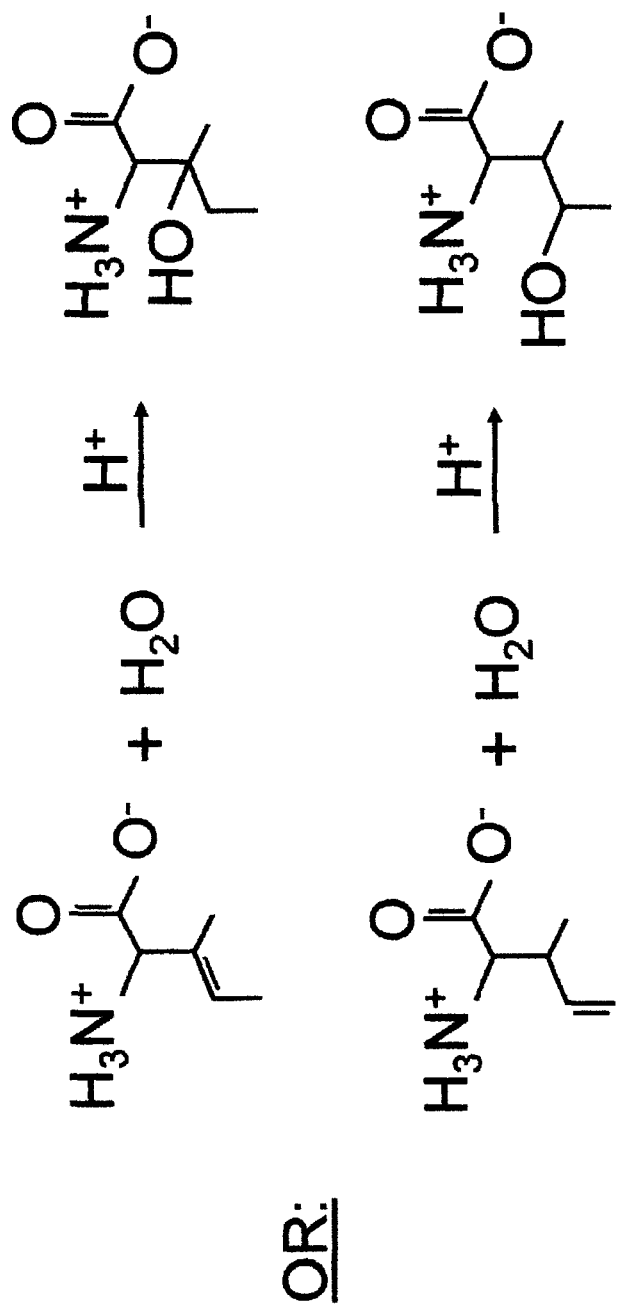
FIG. 3 is a detail view of an embodiment of the disclosure.

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

Detailed reference will now be made to one or more potential embodiments of the disclosure, which are illustrated in FIGS. 1 through 18.

The method and preparation for the delivery of selective small molecule phytochemical based and pharmacologically active media through a cell membrane to enhance food groups for health protection and benefits 100 (hereinafter invention) is a process that is configured for use in delivering a selective small molecule phytochemical based and pharmacologically active media (hereinafter selective small molecule P and P active media 101) through a cell membrane. The selective small molecule P and P active media 101 is a chemical substance that has a biochemical or physiological effect on a biological organism. By small molecule is meant that the pharmacologically active media has a molecular weight of less than 1000 Daltons. The invention 100 delivers the selective small molecule P and P active media 101 through the cell membrane. The invention 100 delivers the selective small molecule P and P active media 101 through the cell membrane by taking advantage of the cell's metabolic activity. Specifically, the selective small molecule P and P active media 101 attaches to a foodstuff 110 that is brought through the cell membrane as part of the cell's normal metabolic activity.

The invention 100 comprises preparing a modified foodstuff 110 such that: a) the foodstuff 110 comprises one or more nutrients; b) one or more nutrients selected from the foodstuff 110 can receive the selective small molecule P and P active media 101; c) attaching one or more selective small molecule P and P active media 101 to one or more selected nutrients; such that, d) the modified foodstuff 110 is enhanced and edible.

The combination of the selected nutrient and the selective small molecule P and P active media 101 is selected such that when the selected nutrient is brought through the cell membrane as part of the cellular metabolic process, the selective small molecule P and P active media 101 is also brought through the cell membrane with the selected nutrient. The selective small molecule P and P active media 101 attaches to the one or more selected nutrients such that once within the cell, enzymes naturally found within the cell will cleave the selective small molecule P and P active media 101 from the selected nutrient such that both the selected nutrient and the selective small molecule P and P active media 101 are available for use within the cell.

The invention 100 can be further supplemented by the introduction of supplemental detoxifiers, prebiotics, and probiotics into the foodstuff 110 after the attachment of the selective small molecule P and P active media 101 to the selected nutrient at the molecular level. The supplemental detoxifiers, prebiotics, and probiotics are selected to enhance the activity of the selective small molecule P and P active media 101 within the cell.

The selected nutrient is a chemical compound that forms an energy source that supports the metabolic activity of the cell. The selected nutrient is derived from the foodstuff 110. The selected nutrient is selected from the group consisting of an amino acid 111 (protein), a carbohydrate 112, and a lipid 113. The lipid 113 is selected from the group consisting of a fatty acid, a tri-ester, and a steroid.

The amino acid 111 is a molecule used by the cell both as an energy source and to build proteins. A protein is a polymer chain of amino acids 111 formed from catalytic reactions (RNA polymerases) to create the amino acid 111 polymer chain. The cell further uses various protein structures as catalysts and to form mechanical structures within the cell. The carbohydrate 112 is used by the cell as a source of energy. The carbohydrate 112 is the most energy efficient energy source available to the cell. The lipid 113 is a high energy density molecular structure used to store excess energy for future use by the cell.

The selective small molecule P and P active media 101 is a phytochemical that is known to be biologically active. The selective small molecule P and P active media 101 is selected from the group consisting of terpenoids 121, flavonoids 122, polyphenols 123, and polyacetylenes 124. The terpenoids 121, the flavonoids 122, the polyphenols 123, and the polyacetylenes 124 are defined in greater detail elsewhere in this disclosure.

Terpenoids 121 are a large and diverse group of organic chemicals naturally produced by many plants including the *cannabis* plant. Terpenoids 121 represent the largest and the most diverse class of beneficial plant chemicals. To date over 40,000 individual terpenoids 121 exist and new ones are discovered every year. Cumulative research suggests terpenoids 121 may help prevent metabolic disorders, fight cancer and cardiovascular diseases, exert anti-aging benefits and boost the immune system. Terpenoids 121 are responsible for wide varieties of flavors and aromas making them a sought-after commodity by the flavor and the fragrance industry. The carotenoids are a class of terpenoids 121 that are organic pigments providing characteristic bright colors of fruits and vegetables.

The polyphenols 123 are a class of natural organic chemicals characterized by the presence of multiple phenolic rings. The polyphenols 123 are a class of phytochemical that further comprises lignans. Lignans comprises a polyphenol 123*ic* structure that contains dimer of two polyphenol 123 structures. The lignans are antioxidants known to be anti-carcinogenic and for their ability to boost the immune system. The molecule reservatrol 142 (approx. 230 Daltons) is a lignin known for cardiovascular benefits and for influencing the function of hormones within a body.

The flavonoids 122 are antioxidants that include, but are not limited to, the flavanols the anthocyanins, and the isoflavones. The flavanols are based on the flavone backbone and are known to have cardiovascular benefits. The anthocyanins are also based on the flavone backbone are known to support liver function and reduce blood pressure. The isoflavones are based on the isoflavone backbone are a class of antioxidants known to influence the functions of hormones within a body and that support bone growth. Isoflavones are also known to enhance natural production of steroids in a cell.

The polyacetylenes 124 are a class of chemicals that contain a polymer that can theoretically be formed from alkynes. The polyacetylene 124 structure commonly occurs in naturally occurring fatty acids.

One advantage of invention 100 is that the selection of both the selected nutrient and the selective small molecule P and P active media 101 can be targeted such that the selective small molecule P and P active media 101 is more likely to be introduced to cells requiring the selective small molecule P and P active media 101.

The benefits of invention 100 can be made clearer through the presentation of examples. The examples presented in the following paragraphs are exemplary in nature and should not necessarily be construed as preferred or advantageous over other implementations. These examples are provided for the purposes of simplicity and for clarity of exposition of the disclosure and are not intended to limit the scope of the appended claims but are instead provided to enable persons skilled in the art to practice the disclosure.

The first example targets the amino acid 111 isoleucine 131 (CAS 73-32-5 and ILE). Isoleucine 131 is an essential amino acid 111 that is only available to the cells through the diet. Isoleucine 131 is considered a hydrophobic amino acid 111. Isoleucine 131 is transported through the cell membranes through capillary diffusion. By attaching the selective small molecule P and P active media 101 to the residue 132 of isoleucine 131, the selective small molecule P and P active media 101 will be drawn through the cell membranes with the isoleucine 131.

The first example will assume that the selective small molecule P and P active media 101 is curcumin 141 (CAS 458-37-2 approximately 370 Daltons). Curcumin 141 is a lignan that comprises a dual ketone alkene structure terminated on each end by identical ether-phenol structures. The dual ketone alkene structure comprises two carbon-carbon double bonds. When curcumin 141 is present within a cell, the two carbon-carbon double bonds act as reduction sites that can be oxidized by an oxidizer such as bisphenol-A. This allows the curcumin 141 to perform the function of an antioxidant within the cell.

The attachment of the curcumin 141 directly to the residue 132 of the isoleucine 131 provides two immediate advantages. First, because isoleucine 131 is an essential amino acid 111, isoleucine 131 is continuously required by all cells in the body and is regularly transported through cell membranes to support metabolic processes. By attaching the curcumin 141 to the isoleucine 131, a patient can be confident that a dose of curcumin 141 will be distributed evenly through all the cells in the body. Second, because isoleucine 131 passes through the cell membrane using capillary diffusion, the attachment of curcumin 141 to the isoleucine 131 allows for the curcumin 141 to also pass through the cell membrane using capillary diffusion. This is a significant advantage over other active chemical mechanisms used to transport molecules through the cell membrane.

Once inside the cell, the curcumin 141 and the isoleucine 131 must be separated. In the first example, this is accomplished by enzymes commonly found within the cell metabolism of the human body. One enzyme suitable for this task is alkylglycerol monooxygenase (EC 1.14.16.5). Alkylglycerol monooxygenase is a relatively nonspecific etherase that reduces ether bonds to fatty acids and glycerols. Once inside the cells, alkylglycerol monooxygenase will separate the isoleucine 131 from the curcumin 141 allowing each molecule to perform its function independently.

After cleavage by the alkylglycerol monooxygenase, the isoleucine 131 returns to its original and intended structure that allows the isoleucine 131 to be subsequently incorporated into a protein using the natural metabolic processes.

After cleavage by the alkylglycerol monooxygenase, the two carbon-carbon double bonds of the curcumin 141 remain intact to form reduction sites that can be oxidized by an oxidizer such as bisphenol-A. After the oxidization of the reduction sites, the molecule formed by the combination of the curcumin 141 and the oxidizer is excreted through the cell membrane using normal metabolic processes and thereby detoxifying the cell.

The following three paragraphs describe the stoichiometry of the oxidation process. Specifically, after the separation of the isoleucine 131 and the curcumin 141, one can express the scavenging/neutralization of oxygen free radical in the following manner.

While the majority of the isoleucine 131 is converted to proteins by enzyme catalysts, some isoleucine 131 reacts with the Bisphenol A 152 (CAS 80-05-7). The bisphenol A 152 is a potent carcinogen. The bisphenol A 152 reacts with Isoleucine 131 and forms a powerful oxidizing agent (also referred to as $O^*$) that damages the cell membranes. This is expressed in a first stoichiometric equation: Isoleucine 131 (1 Kg mole=131 Kg)+Enzymes (catalyst)+Bisphenol A 152 (10 gm mole=2280 gm)=Proteins (2 Kg mole=130,500 gm or 130.5 Kg)+nutrients (100 gm)+Free radical $O^*$ attached to cell membranes (10 gm mole=160 gm of $O^*$)+Unreacted Bisphenol (520 gm).

Curcumin 141, is a terpenoid 121 found in turmeric. Curcumin 141 is a powerful anti-oxidant that scavenges and neutralizes the $O^*$ and prevents the cell membranes from damaging oxidative degradation. This is expressed in a second stoichiometric equation: 10 gm mole (160 gm) of $O^*$+2 gm mole (368 gm/mole×2=736 gm) of Curcumin 141=Zero gm of $O^*$ (cell membranes free from free radical $O^*$)+576 gm of unreacted curcumin 141.

The effectiveness of the above example can be enhanced with the use of extra-stoichiometric amounts of curcumin 141 (more than 100% of the theoretical amount) which ensures complete scavenging of the $O^*$ and prevailing a condition that the reaction does not go to the reverse direction.

The applicants now address the specific process of attaching the curcumin 141 to the isoleucine 131. This is accomplished by: a) forming a double bond to create an alkene structure in the residue 132 of the isoleucine 131 (Steps 1A and 1B); b) converting the alkene structure of the isoleucine 131 residue 132 into a hydroxyl 162 group in the original alkane structure isoleucine 131 residue 132 (Step 2); and c) creating an ester bond between the hydroxyl 162 group on the isoleucine 131 residue 132 and a hydroxyl 162 group selected from the group consisting of a hydroxyl 162 group of one of the two ether-phenol terminal groups of the curcumin 141 (Step 3 Scenario 1).

Specifically, the double bond can be formed by subjecting the isoleucine 131 to a halogenation reaction with bromine 161 (Step 1A). The use of bromine 161 is preferred because of the selectivity of bromine 161 for secondary carbons in halogenation reactions. Once the isoleucine 131 is halogenated with bromine 161, the double bond is created by subjecting the bromated isoleucine 131 to a water solution of high pH (Step 1B).

Once the double bond is created in the isoleucine 131, the double bonded isoleucine 131 is then subjected to a hydrogenation reaction in a low pH environment to create a hydroxyl 162 (alcohol) functional group within the residue 132 of the isoleucine 131 (Step 2).

Finally, the hydroxyl 162 formed by the residue 132 of the isoleucine 131 can be bonded with a hydroxyl 162 selected from the group consisting of one of the two ether-phenol terminal groups of the curcumin 141 using an ether bond formed by condensation synthesis in a heated acidic environment (Step 3). These reactions are shown in the FIGS. 1, 2, 3, and 4.

Figure 4:
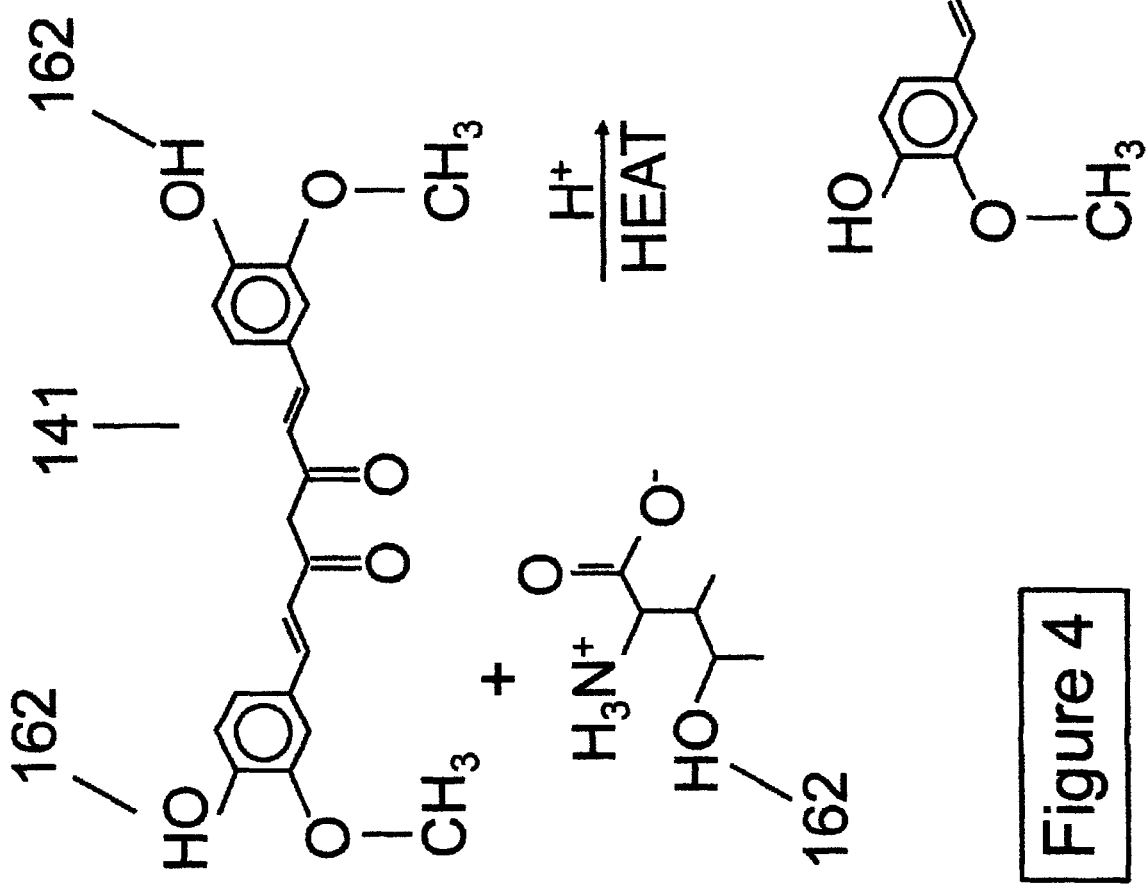
FIG. 4 is a detail view of an embodiment of the disclosure.
Figure 5:
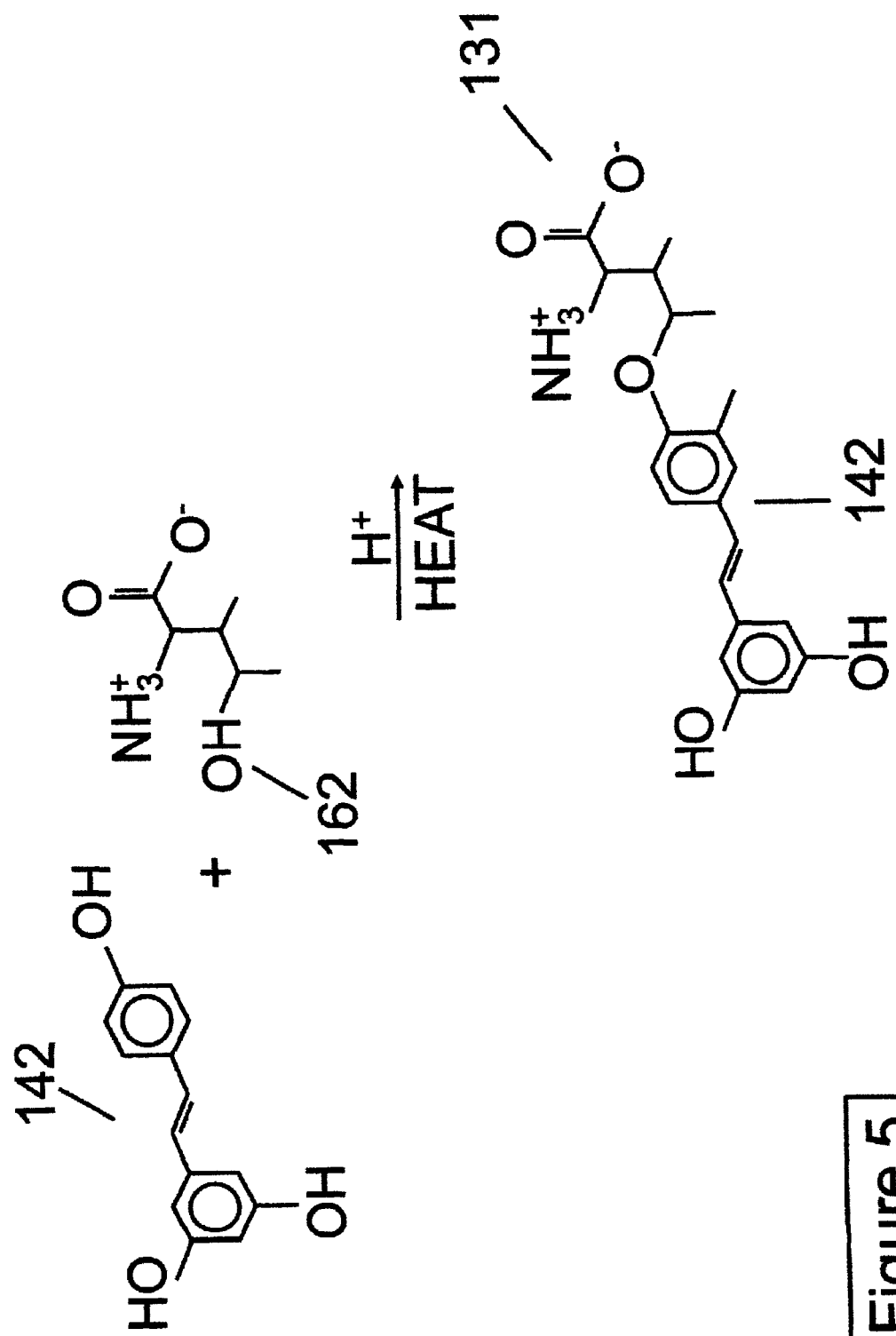
FIG. 5 is a detail view of an embodiment of the disclosure.

The applicant would point out that Step 3 can be extended to alternate scenarios. In a second scenario, shown in FIG. 5, the process of Step 3 will attach the polyphenol 123 resveratrol (CAS 501-36-0) to isoleucine 131 in a manner that is identical to the attachment of curcumin 141 to isoleucine 131. This curcumin 141-isoleucine 131 reaction is shown in FIG. 4.

The following additional examples illustrate the functionality of invention 100 in providing protection against many diseases.

Figure 6:
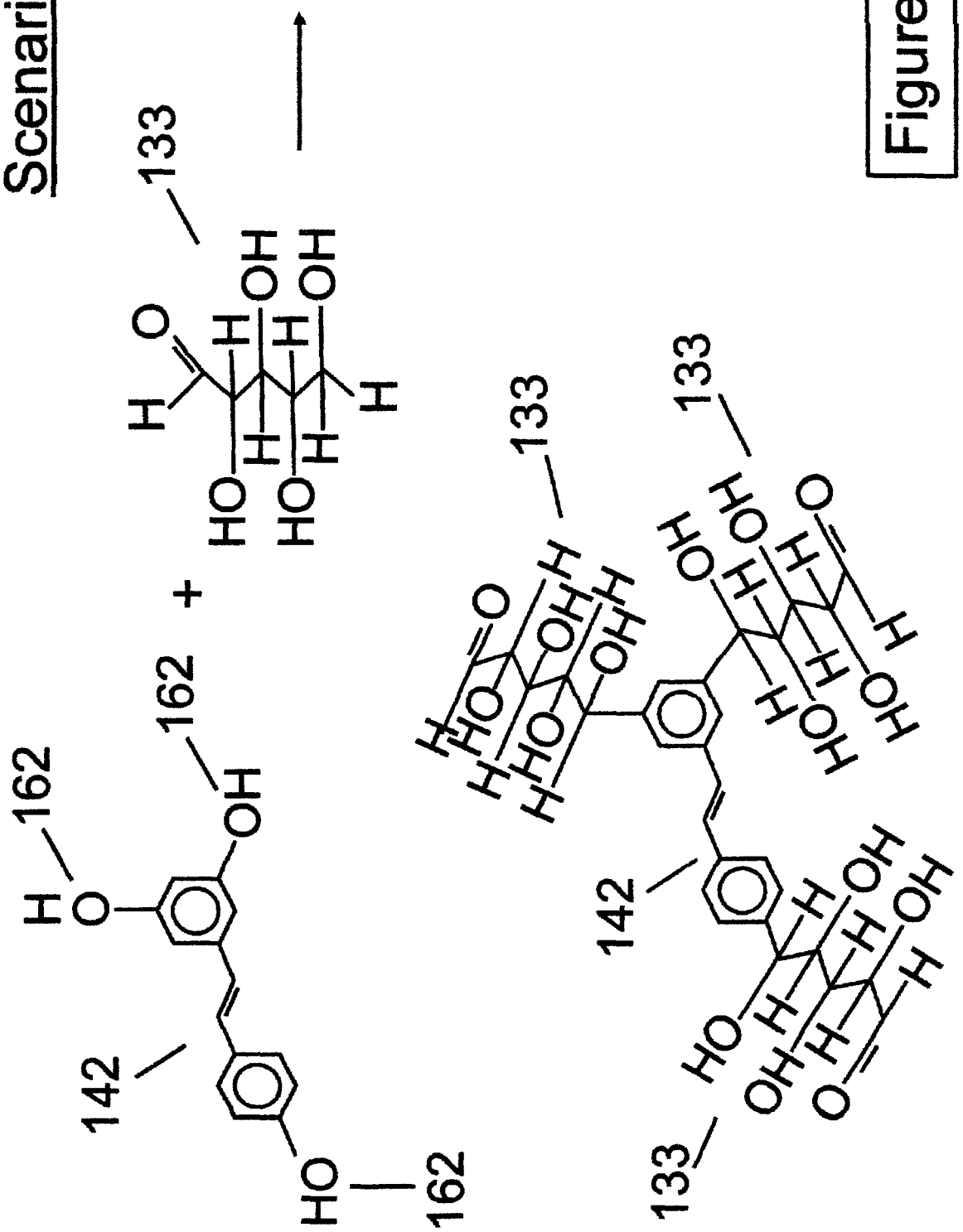
FIG. 6 is a detail view of an embodiment of the disclosure.

In a third potential scenario, reservatrol 142 attaches to a carbohydrate 112. By attaching resveratrol 142 to a carbohydrate 112, the well-known the cardiovascular benefits of reservatrol 142 are distributed globally without the preferential intake of the prior two scenarios. As shown in FIG. 6, up to three carbohydrates 112 can be attached to the three hydroxyl 162 groups of the resveratrol using standard dehydration techniques. The example shown attaches pentose 133 monosaccharides to the resveratrol.

Figure 7:
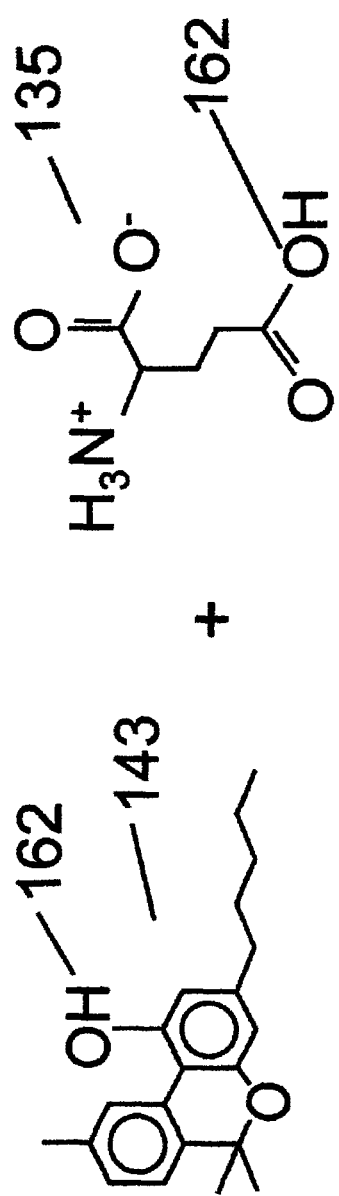
FIG. 7 is a detail view of an embodiment of the disclosure.
Figure 7:
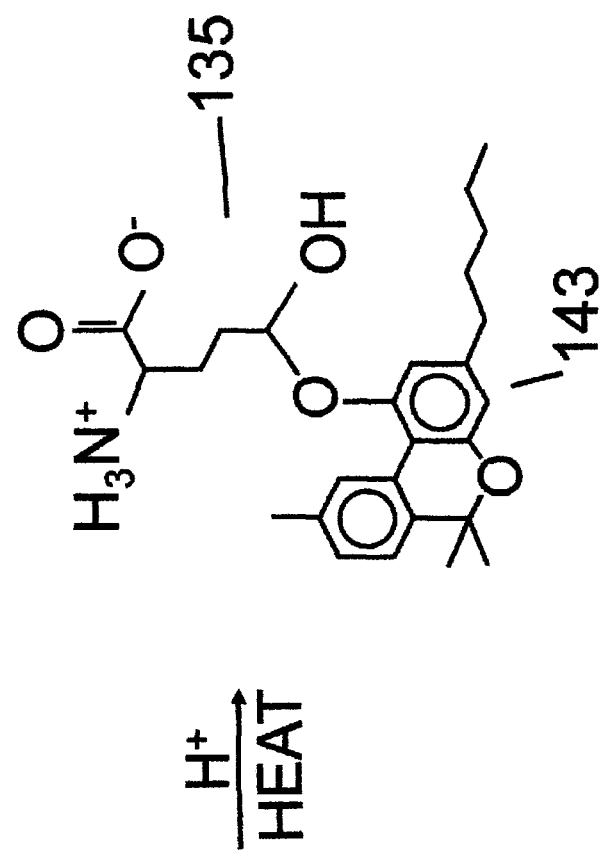
Figure 8:
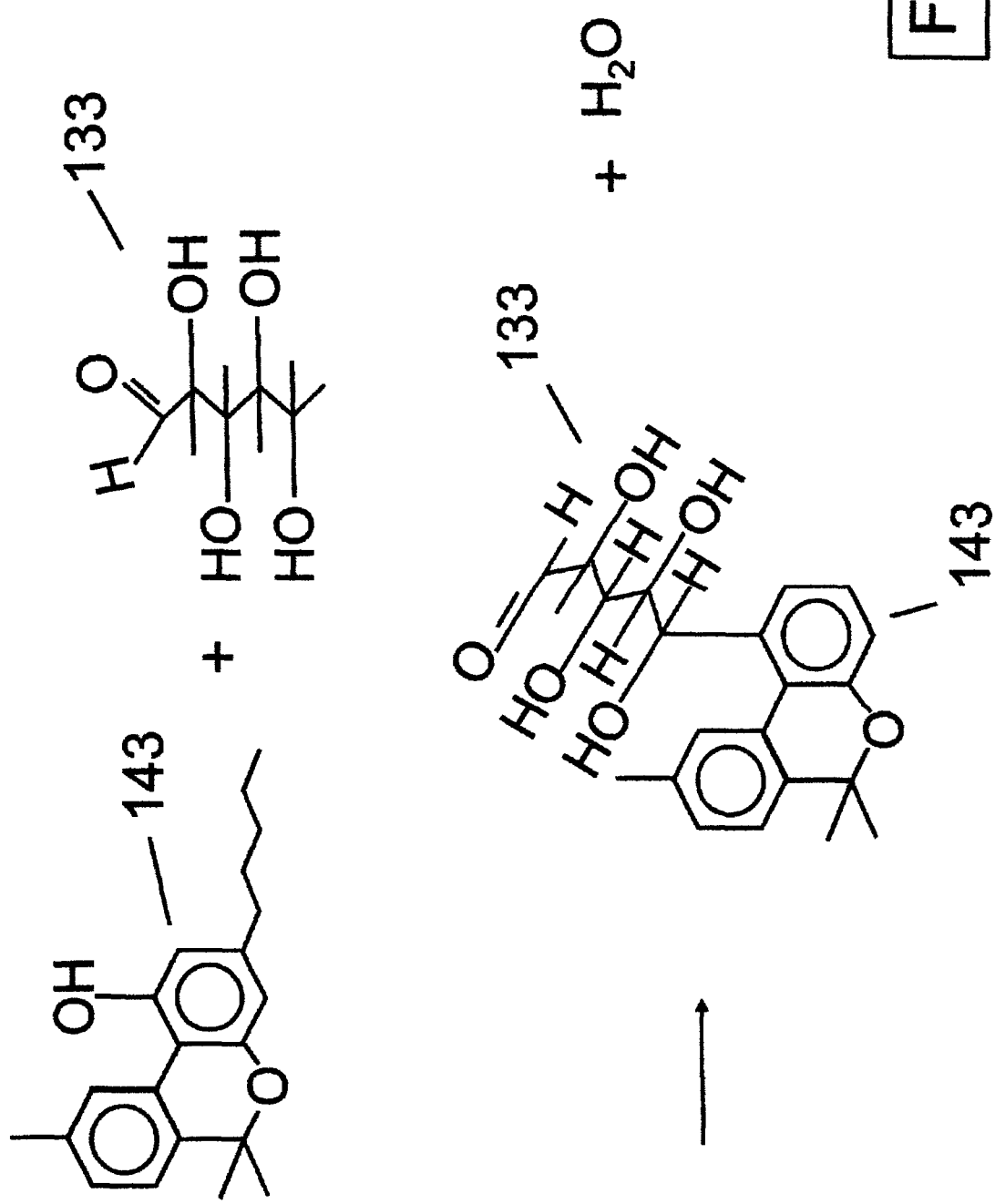
FIG. 8 is a detail view of an embodiment of the disclosure.

Cannabinol 143 (CAS 1972-08-3) is presented as a fourth potential scenario of the functionality presented in this disclosure. Cannabinol 143 is a polyphenol 123 derived from *cannabis*. Cannabinol 143 is a selective small molecule (approx. 315 Daltons) known for reducing inflammation within a body. Glutamic acid 135 (CAS 56-86-0 GLU also referred to a Glutamate) is an amino acid 111 that is statistically more likely to be found in protein structures associated with the healing process. By attaching the hydroxyl 162 group of the cannabinol 143 to the glutamic acid 135, the natural metabolic processes of the cells within the injured portion biological process will naturally intake more cannabinol 143 (relative to uninjured cells) as the cell preferentially draws glutamic acid 135 into the cell membrane. This provides reduces inflammation as the injured cells are repaired. The chemical process to accomplish this is similar to Step 3, and is identified as scenario 4. This reaction is shown in FIG. 7.

Cannabinol 143 is again presented in a fifth potential scenario of this functionality. In this scenario, that cannabinol 143 attaches to a carbohydrate 112 to facilitate the global distribution of the cannabinol 143 molecule. As shown in the attached figure, a single carbohydrate 112 can be attached to hydroxyl 162 groups using standard dehydration techniques. The example shown in FIG. 8 attaches a pentose 133 monosaccharide to the cannabinol 143.

Malvidin 144 (CAS 7228-78-6) is presented as a sixth potential scenario of the functionality presented in this disclosure. Malvidin 144 (approx. 285 Daltons) is an anthocyanin derived from the flavonoids 122. Malvidin 144 promotes bone healing and growth. In the sixth potential scenario, malvidin 144 attaches to a lipid 113. More specifically, the malvidin 144 attaches to palmitic acid 134 (CAS 57-10-3). The applicants anticipate that the normal metabolic requirement of the cell would result in a substantial proportion of the consumed malvidin 144 to be stored as an energy reserve creating a slow release of malvidin 144 over a longer period time. This will provide a steady supply of malvidin 144 throughout slow healing and growth of the bones and cartilages.

Figure 9:
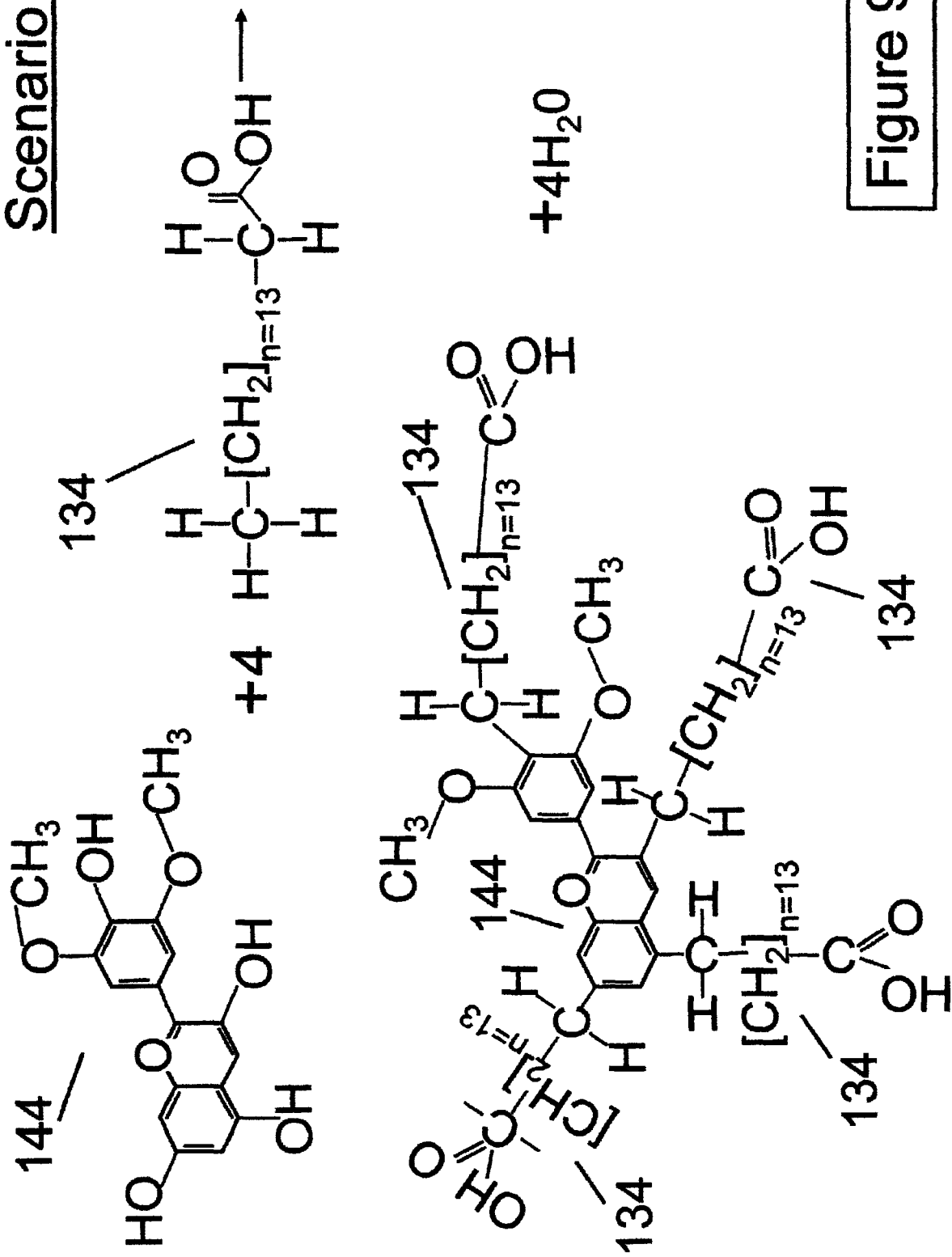
FIG. 9 is a detail view of an embodiment of the disclosure.

As shown in FIG. 9, up to three palmitic acid 134 molecules can be attached to the three hydroxyl 162 groups of the malvidin 144 using standard dehydration techniques. While palmitic acid 134 is a fatty acid, the applicants note that the dehydration technique used is equally applicable to other lipid 113 structures including tri-esters. The applicants believe that these standard dehydration techniques can be applied to lipids 113 without undue experimentation.

Figure 10:
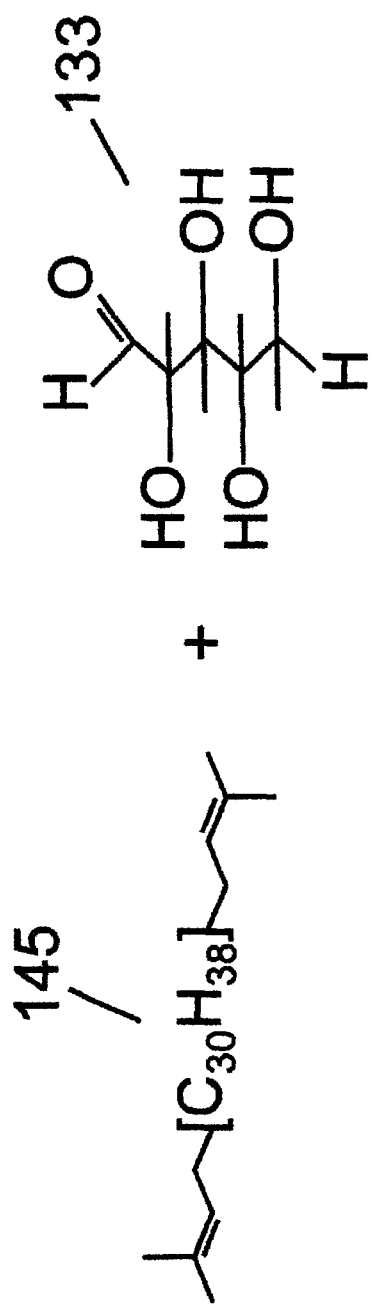
FIG. 10 is a detail view of an embodiment of the disclosure.
Figure 10:
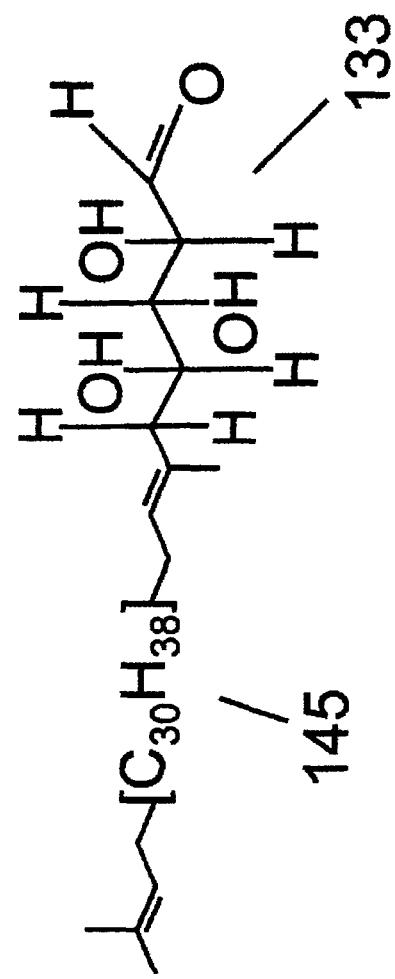
Figure 11:
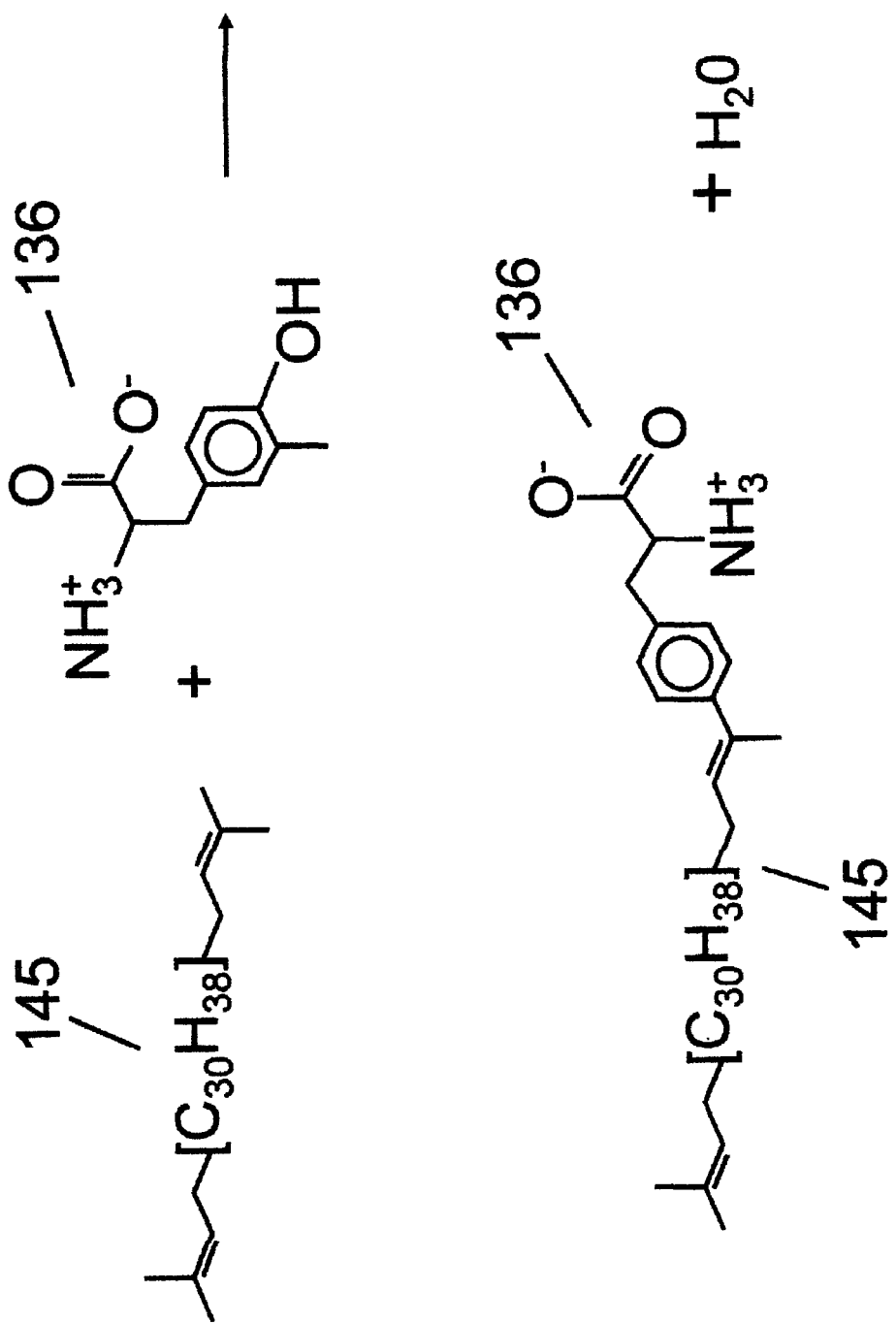
FIG. 11 is a detail view of an embodiment of the disclosure.
Figure 12:
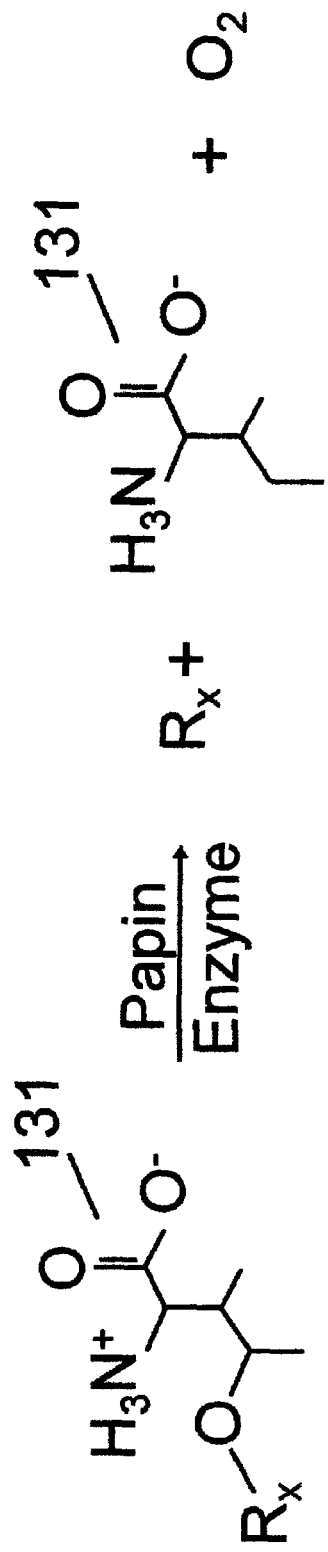
FIG. 12 is a detail view of an embodiment of the disclosure.

Lycopene 145 (CAS 502-65-8) is presented as a seventh potential scenario of the functionality presented in this disclosure. Lycopene 145 is a polyacetylene 124 commonly found in carrots. The lycopene 145 in an anti-oxidant with known health correlations that include, but are not limited to, cholesterol management benefits, cardiovascular benefits, immunity boosting properties, hypertension benefits, retinal benefits, and diabetes management benefits. As shown in FIG. 10, a single lycopene 145 can be attached to a hydroxyl 162 group on a carbohydrate 112 using standard dehydration techniques. The example shown attaches a pentose 133 monosaccharide to the lycopene 145.

Lycopene 145 is presented as an eighth potential scenario of the functionality presented in this disclosure. As shown in the FIG. 11, a single lycopene 145 can be attached to the hydroxyl 162 group on the amino acid 111 tyrosine 136 (60-18-4 TYR) using standard dehydration techniques.

The applicant anticipates that the processes described above can be incorporated into the chemistry commonly found in the food processing industry. For example, the cannabinol 143 can be bonded to the glutamic acid 135 as part of the cheese making process. The reservatrol 142 can be bonded to a sugar substrate that is used to sweeten a soft drink or sweeten a baked good. The malvidin 144 can be incorporated into the fatty acids found in milk (a source of calcium) before making ice cream.

The applicant observes nature provides thousands of phytochemicals and sources of phytochemicals that can be incorporated into invention 100. The applicant further observes that there is a broad and deep literature documenting the benefits of these phytochemicals.

To document the above observations, the applicant includes Table 1 with this disclosure (presented below).

TABLE 1

Phytochemical Sources, Selective Groups, Boosters, and Target Protection

| SL NO | Phytochemical Source | Phytochemical Group | Food Group to be Enhanced | Additional Booster | Target Protection | Other Benefits |
|---|---|---|---|---|---|---|
| 1 | Red Grape Skin Pomegranate Thyme | Flavanoids Cartenoids Terpenoids Polyphenols | Protein Carbohydrate Lipid | BSDM* Prebiotic Probiotic | Cardiovascular | Boosts Immunity |
| 2 | Astragulas Barley Turmeric Root | Cartenoids Terpenoids Polyphenols | Protein Carbohydrate Lipid | BSDM* Prebiotic Probiotic | Cancer Immunity | Boosts |
| 3 | Cannabis Hemp Boswellia Serrata | Cartenoids Terpenoids Polyphenols | Protein Carbohydrate Lipid | BSDM* Prebiotic Probiotic | Arthritis + Joint and Muscle Pain | Boosts Immunity |

TABLE 1-continued

Phytochemical Sources, Selective Groups, Boosters, and Target Protection

| SL NO | Phytochemical Source | Phytochemical Group | Food Group to be Enhanced | Additional Booster | Target Protection | Other Benefits |
|---|---|---|---|---|---|---|
| 4 | Ginkgo Biloba Soybean Clove | Flavanoids Polyphenols | Protein Carbohydrate Lipid | BSDM* Prebiotic Probiotic | Alzheimer | Boosts Immunity |
| 5 | Triphala Cinnamon Almond Walnut | Flavanoids Polyphenols | Protein Carbohydrate Lipid | BSDM* Prebiotic Probiotic | Diabetes | Boosts Immunity |
| 6 | Milk Thistle Neem Leaf | Flavanoids Cartenoids Terpenoids | Protein Carbohydrate Lipid | BSDM* Prebiotic Probiotic | Hepatitis | Boosts Immunity |
| 7 | Licorice Root Fennel Anise | Flavanoids | Protein Carbohydrate Lipid | BSDM* Prebiotic Probiotic | Gastritis Indigestion | Boosts Immunity |
| 8 | Purple Corn (leaf and kernel) Eggplant Chokeberries | Anthocyanins (Flavanoids - Malvidin) | Protein Carbohydrate Lipid | BSDM* Prebiotic Probiotic | Bone & Cartilage | Boosts Immunity |
| 9 | Deep Purple Carrot | Polyacetylenes | Protein Carbohydrate Lipid | BSDM* Prebiotic Probiotic | Inflammation | Boosts Immunity |

B - Burdock Root
S - Stinging Nettle
D - Dandelion
M - Milk Thistle
Prebiotics: Jerusalem Artichoke, Asparagus, Jicama
Probiotics: Yogurt, Kefir, Sauerkraut, Kimchi Table 1 shows selected sources of phytochemicals and four (4) antioxidant groups and the food groups (flavonoids 122, carotenoids/terpenoids 121, polyphenols 123, and polyacetylenes 124) and the selected nutrients that form the substrate to be enhanced. Table 1 also shows supplemental detoxifiers, prebiotics, and probiotics that will further enhance the effectiveness and functionality of the phytochemical source when used in conjunction with the cellular attachment of the phytochemical source. The protection provided against various diseases by the phytochemicals and antioxidants are also stated.

It is to be noted that Table 1 provides only a few examples of the potential protection and immune system boosting against certain diseases provided by the phytochemicals. There are numerous phytochemicals and antioxidants that can provide health protection and immune system boosting. Table 1 is provided for the purposes of simplicity and for clarity of exposition of the disclosure and is not intended to limit the scope of the appended claims. Table 1 is instead provided to enable persons skilled in the art to more effectively practice the disclosure.

All foodstuff 110 nutrients (protein/carbohydrate 112/ lipids 113) can be enhanced by various phytochemicals. The enhancement can further be stimulated by adding detoxifiers, prebiotics, and probiotics to the cellular matrix. Like the phytochemicals, the detoxifiers, prebiotics, and probiotics will also attach to the cell membranes and provide protection against many diseases.

As shown in Table 1, phytochemical sources like red grape skin, pomegranate and Thyme tend to provide superior protection against cardiovascular diseases because of such antioxidants as flavonoids 122, terpenoids 121, and polyphenols 123. Sources like astragulus, barley, and turmeric root tend to provide superior protection against cancer because of the presence of antioxidants like beta-glucans and curcuminoids 141. Certain polyphenols 123 and terpenes present in *cannabis* and *Boswellia serrata* tend to provide enhanced protection against arthritis, inflammation and joint/muscle pain. The *cannabis* further provides good protection against inflammation and joint/muscle pain.

The flavonoids 122 and polyphenols 123 in *Ginkgo biloba*, soybean and clove tend to recover the loss of memory associated with Alzheimer. Triphala (an ancient Indian formulation of three natural ingredients) and cinnamon works well for modulating the levels of blood insulin for diabetic patients. The flavonoids 122 and polyphenols 123 are the key antioxidants for modulating insulin. The flavonoids 122 and terpenoids 121 in milk thistle and neem leaves or neem oil provide protection against hepatitis. The flavonoids 122 in licorice root, anise, and fennel seeds help fight gastritis, indigestion and similar ailments.

The root cause of many fatal diseases is inflammation that originates at the cellular level. Controlling inflammation at the cellular level provides synergy for protection against diseases like cardiovascular, cancer, arthritis and joint and muscle pain. Selective phytochemical group like the polyacetylenes 124 can offer excellent protection against inflammation. Deep purple colored carrots are an excellent source of natural polyacetylene 124 that can be incorporated into a food substrate to provide effective protection against inflammation.

The power of all phytochemicals/antioxidants are boosted significantly when detoxifiers, prebiotics, and probiotics are incorporated in the cellular matrix of food groups. Detoxifiers derived from burdock root, stinging nettle, dandelion, and milk thistle are some natural substances that can boost the health protection characteristics of the selected phytochemicals in Table 1. Detoxifiers further cleanse blood and organs like kidney and liver by removing accumulated toxins from the body and provide protection against radiation damage.

The addition of natural prebiotic substances like Jerusalem artichoke, asparagus and jicama and natural probiotic substances like yogurt, kefir, sauerkraut, and kimchi can further stimulate the effectiveness of health protection by striking the proper balance between all physiological variables within a human body.

The above reactions can be controlled within a single reactor. The requirements of the reactor include: a) providing a reaction space 171; b) a heating jacket 172 used for controlling the temperature within the reaction space 171; c) a low speed agitation 173 device used to mix the contents within the reaction space 171; and, d) a pump 174 used to control the pressure within the reactor. The described configuration for the reactor is similar to those used in the food industry.

Figure 13:
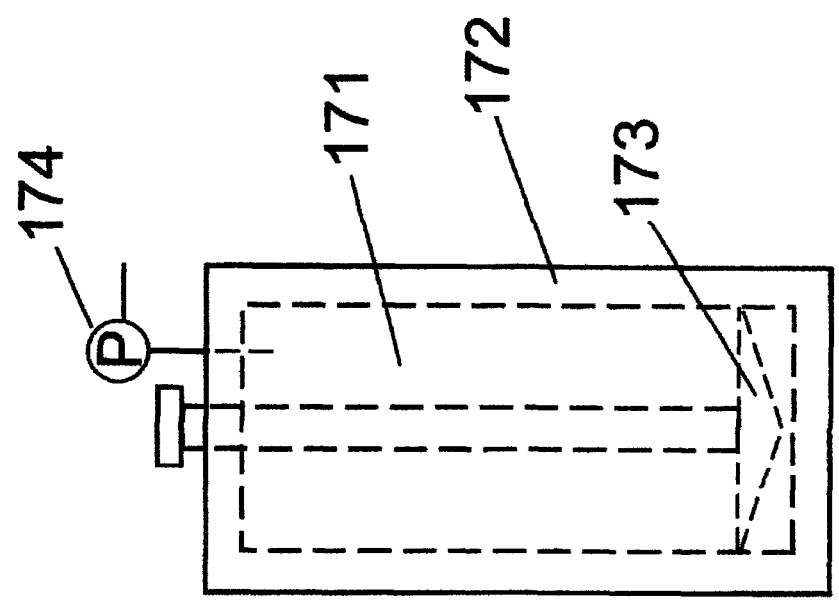
FIG. 13 is a detail view of an embodiment of the disclosure.
Figure 14:
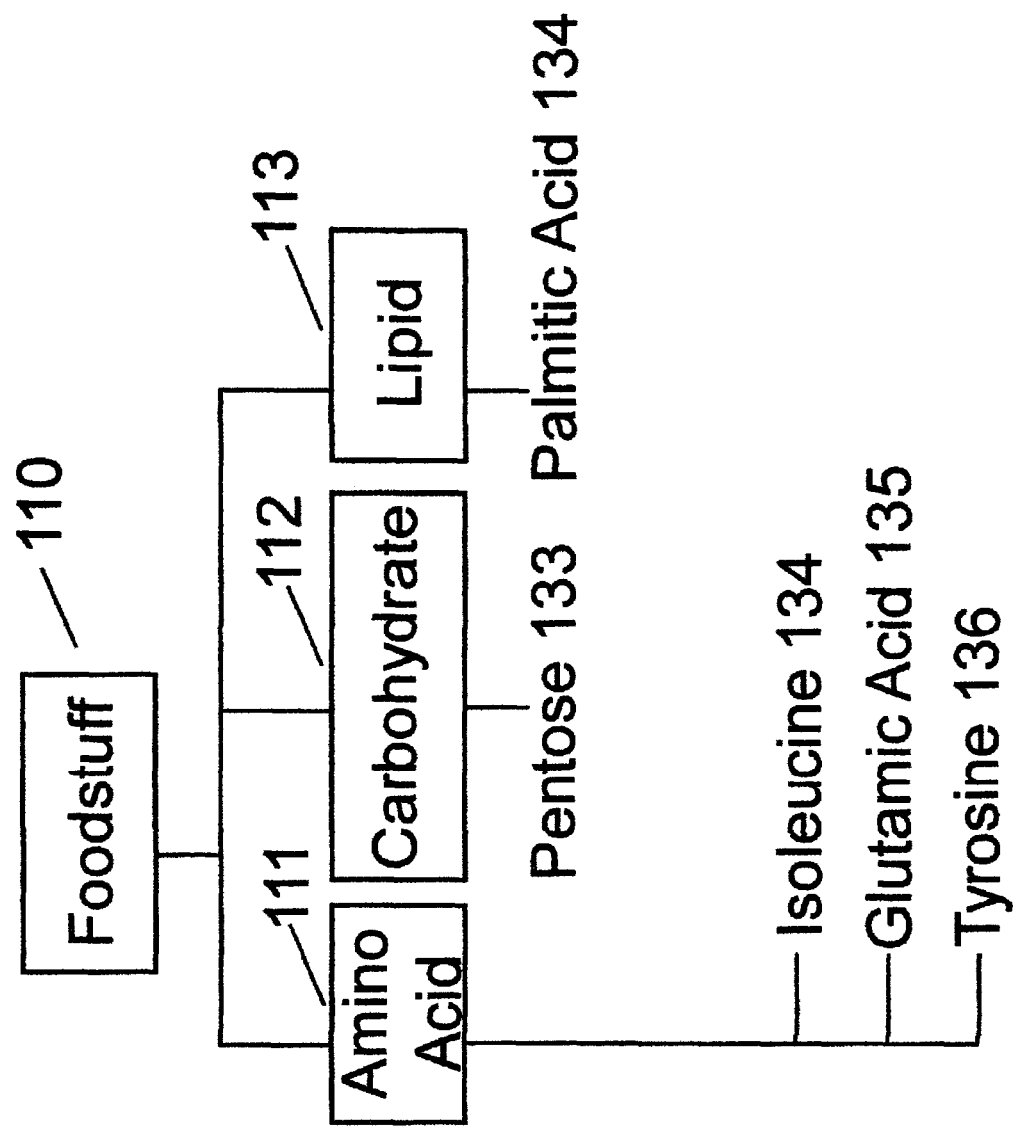
FIG. 14 is a detail view of an embodiment of the disclosure.
Figure 15:
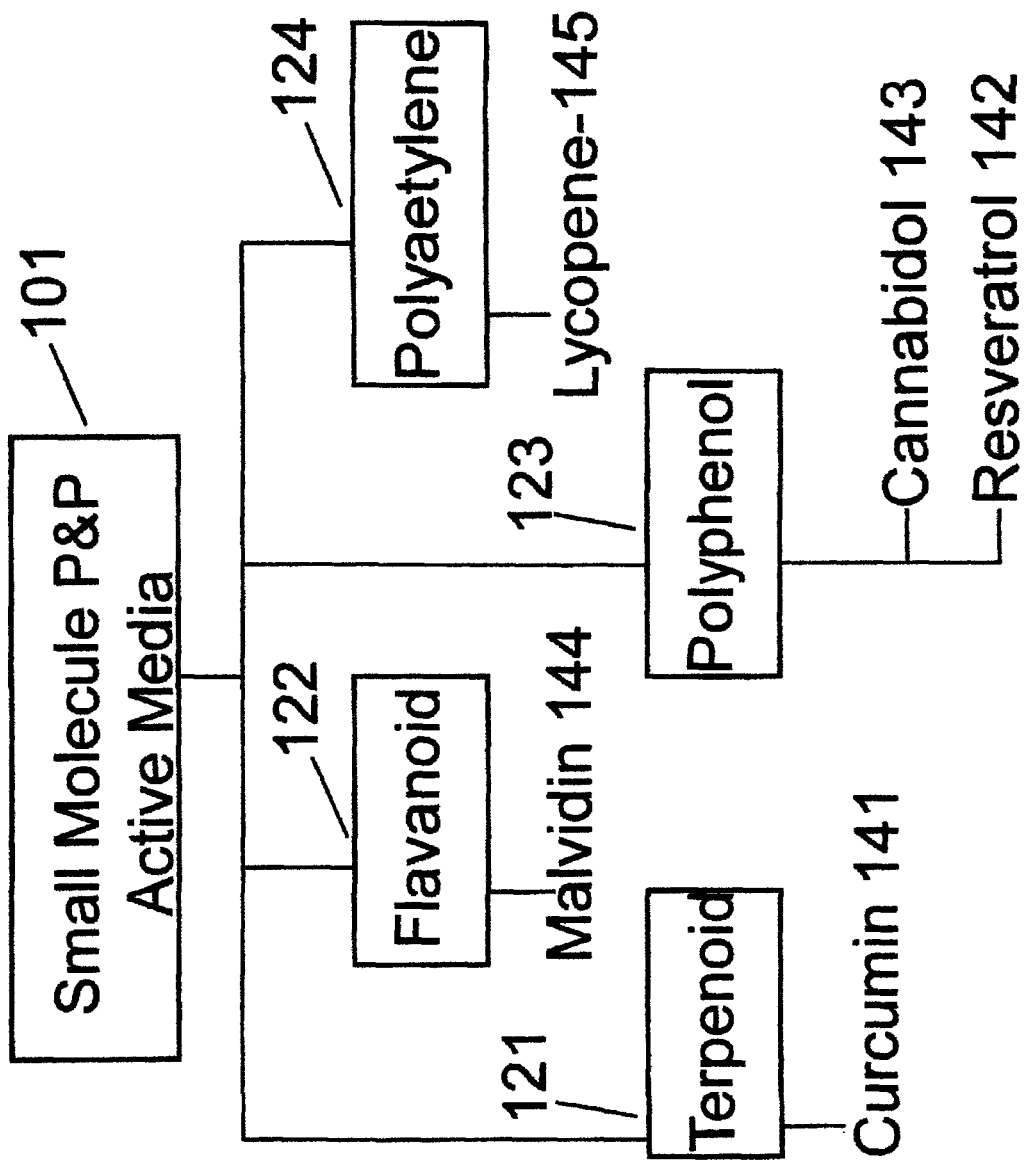
FIG. 15 is a detail view of an embodiment of the disclosure.
Figure 16:
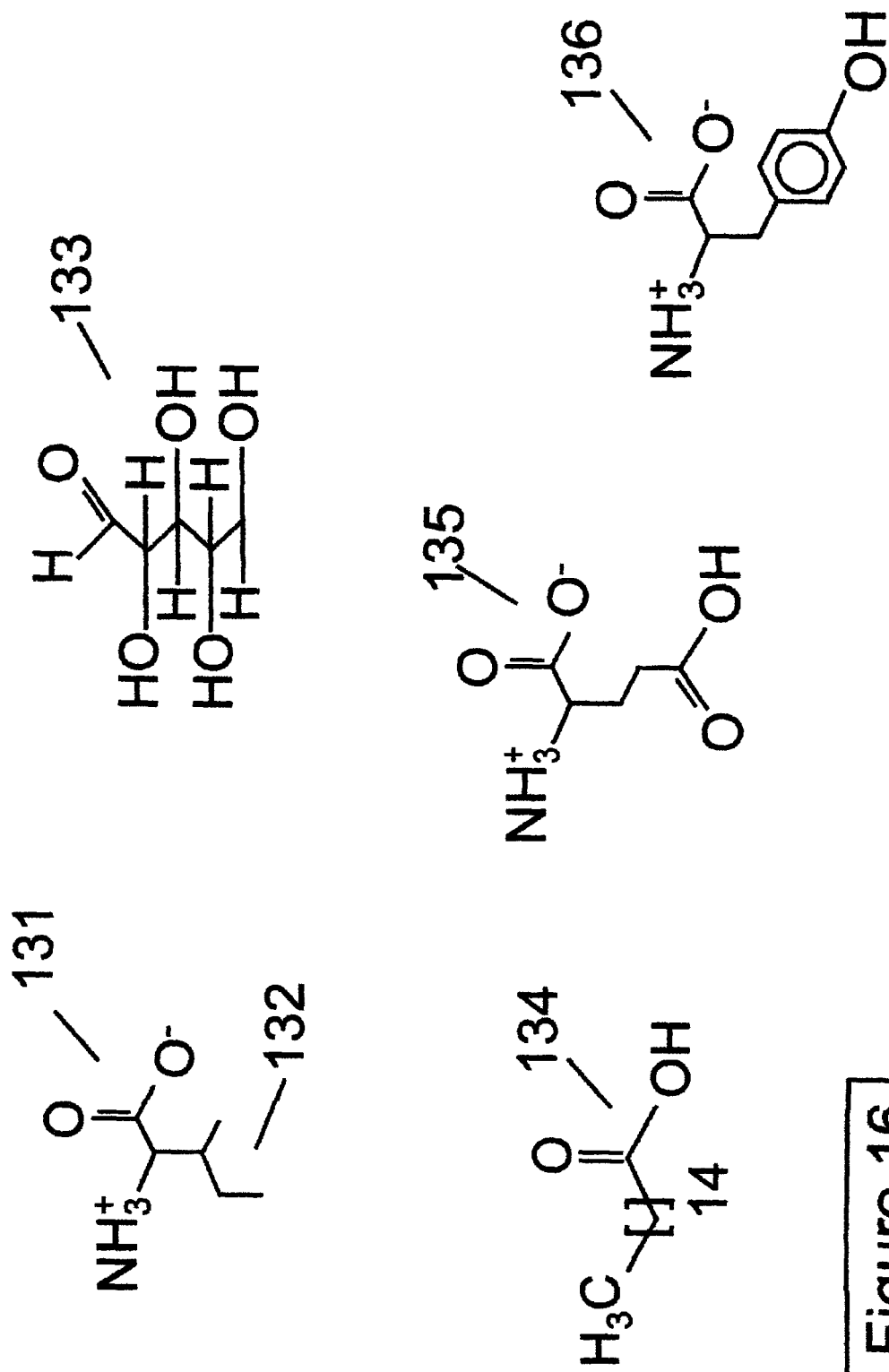
FIG. 16 is a detail view of an embodiment of the disclosure.
Figure 17:
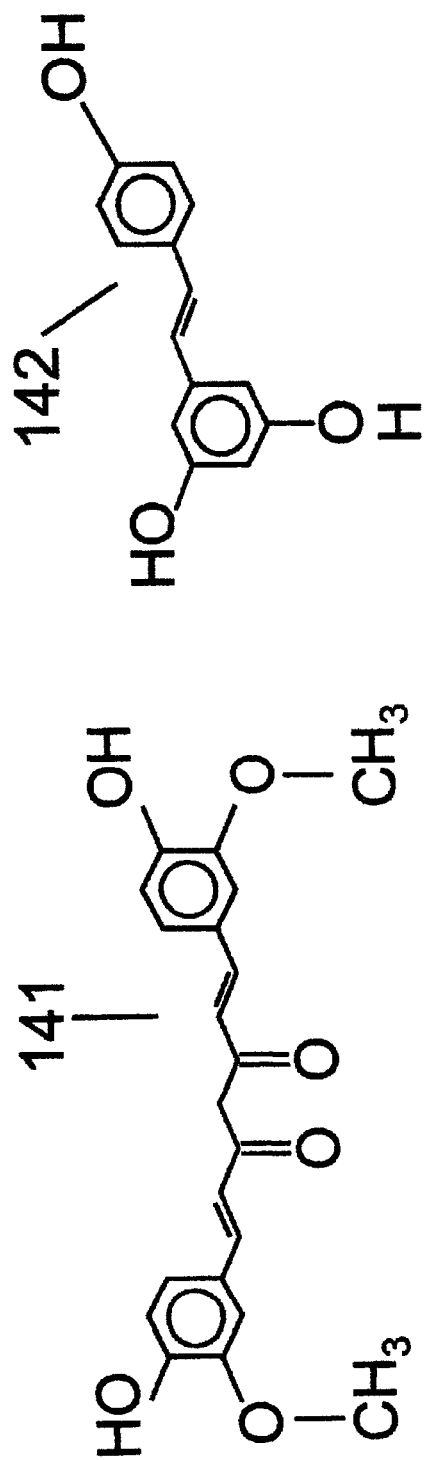
FIG. 17 is a detail view of an embodiment of the disclosure.
Figure 18:
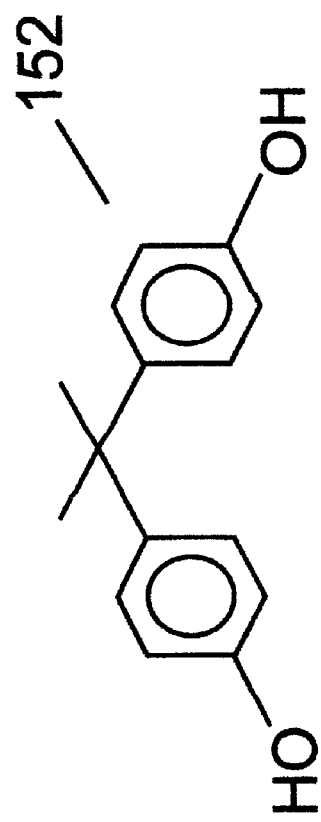
FIG. 18 is a detail view of an embodiment of the disclosure.

FIG. 13 shows a schematic for the reactor that can be utilized to enhance various food groups. The reactor is made of stainless steel with an external jacket for heating. The reactor is fitted with a slow speed agitator for mixing and an external vacuum pump.

The reactor will be operated in sequential batch configurations. The food group to be enhanced will be fed to the reactor and added with the selected phytochemicals. The contents will be heated using low-pressure steam or Dowtherm type of fluid fed through the jacket. Depending on the heat sensitivity of the contents, a vacuum may be applied inside the reactor to facilitate the reaction at a lower reaction temperature. The heating and slow mixing will facilitate capillary diffusion of the phytochemicals and attach to the molecules of the selected nutrient. The mechanisms of molecular attachment are ionic and covalent bondings.

Following enhancement with phytochemicals for 1-2 hours, the reactor contents will be fed with detoxifiers. The sequential batch treatment will be repeated for ½ to 1 hr with moderate heating and slow mixing. This will ensure the detoxifying agents attach to the cell membranes within the food group by capillary diffusion, ionic bonding, covalent bonding, and sorption.

The last step for the process of sequential batch enhancement is adding prebiotic and probiotic agents to the reactor. Like the step for detoxifiers, the pre and the probiotics agents will be heated and agitated for ½ to 1 hr. This will ensure the incorporation of the agents into the cellular matrix of the food group.

The enhanced food contents need to be cooled prior to releasing from the reactor. For rapid cooling, one can circulate cooling water through the jacket. A sample of the enhanced food needs to be taken and analyzed for the concentration of the phytochemicals, the detoxifiers, the prebiotics, and the probiotics.

The following definitions were used in this disclosure.

Biologically Active: As used in this disclosure, biologically active is a term that refers to a substance that contains or is a pharmacologically active media.

Cartenoid: As used in this disclosure, the carotenoid is a phytochemical. The carotenoid is a terpenoid wherein the terpenoid is formed from eight isoprene (CAS 78-79-5) molecules.

Consume: As used in this disclosure, to consume is a verb that refers to the ingestion of a foodstuff by a biological entity. The term consumable refers to a material that can be ingested as a foodstuff.

Detoxification: As used in this disclosure, detoxification refers to a process mitigating the negative biological impact of waste products generated by a cell's metabolic processes. This is accomplished through the use of chemical reactions within the cell and excretion of the waste product from the cell. A detoxifier is a consumed substance that is absorbed through a cell membrane to help with the detoxification process.

Dimer: As used in this disclosure, a dimer refers to the bonding of two or more identical molecules to each other.

Flavonoid: As used in this disclosure, a flavonoid is a phytochemical. The flavonoid comprises a collection of functional groups attached to a chemical backbone selected from the group consisting of: a) the flavone (CAS 525-82-6) chemical group; b) the isoflavone chemical group (CAS 446-72-0); and, c) the neoflavonoid (CAS 51870-64-5) chemical group. Anthocyanins are a common subclass of flavonoid based on the flavone chemical group.

Foodstuff: As used in this disclosure, a foodstuff refers to an edible material that is used as food or a beverage.

Functional Group: As used in this disclosure, a functional group is specific chemical structure that 1) defines the structure of a chemical family; and, 2) determines the properties of the chemical family. Common functional groups include, but are not limited to, aldehydes, alkanes, alkenes, alkynes, alcohols, amides, amines, carboxylic acids, esters, ethers, haloalkanes, haloalkenes, haloalkynes, and ketones. As a practical matter, the intention of this definition is to use the term functional group in the same manner as the term is commonly used in organic chemistry.

Hydroxyl: As used in this disclosure, a hydroxyl refers to a functional group comprising the chemical formulation OH. The hydroxyl is the primary functional group that forms alcohols. When unbound, the hydroxyl is considered an ion and is considered to be a radical.

Lipid: As used in this disclosure, a lipid is an organic molecule that is soluble in nonpolar solvents and other lipids.

Metabolism: As used in this disclosure, metabolism refers to the chemical processes that occur within a living cell.

Pharmacologically Active Media: As used in this disclosure, a pharmacologically active media refers to a chemical substance that has a biochemical or physiological effect on a biological organism.

Phenol: As used in this disclosure, phenol (CAS 108-95-2) refers to a molecule with the chemical structure $C_6H_6O$. The phenol molecule is a cyclic molecule.

Phytochemical: As used in this disclosure, a phytochemical is a pharmacologically active media that is produced in and harvested from a plant. Within this disclosure, a phytochemical comprises a pharmacologically active media selected from the group from: a) the flavonoid chemical group; b) the terpenoid chemical group (including the carotenoid chemical subgroup of the terpenoid chemical group); c) polyphenol chemical group; and, d) the polyacetylene chemical group.

Polyacetylene: As used in this disclosure, a polyacetylene is a phytochemical. The polyacetylene comprises a collection of functional groups attached to a chemical backbone that is formed from, or contains, one or more chains built from the $(C_2H_2)_n$ polymer where $n >= 2$.

Polyphenol: As used in this disclosure, a polyphenol is a phytochemical. The polyphenol comprises a collection of functional groups attached to a chemical backbone formed from two or more phenol (CAS 108-95-2) molecules. A lignan refers to a dimer containing two or more identical molecules that contain a phenol.

Prebiotic: As used in this disclosure, a prebiotic is a consumed substance that is required by a probiotic to provide one or more health benefits. This definition is intended to be consistent with the International Scientific Association for Probiotics and Prebiotics 2016 definition of prebiotic.

Probiotic: As used in this disclosure, a probiotic is a living microorganism that provides one or more health benefits when administered to a patient. This definition is intended to be consistent with the WHO 2005 definition of probiotic.

Terpenoid: As used in this disclosure, a terpenoid is a phytochemical. The terpenoid comprises a collection of functional groups attached to a chemical backbone of a terpene. The terpene is a chemical structure formed from an integer number of isoprene (CAS 78-79-5) molecules. The functional groups attached to the terpenoid will always include at least one hydroxyl (alcohol) group.

With respect to the above description, it is to be realized that the optimum dimensional relationship for the various components of the invention described above and in FIGS. 1 through 18 include variations in size, materials, shape, form, function, and manner of operation, assembly and use, are deemed readily apparent and obvious to one skilled in the art, and all equivalent relationships to those illustrated in the drawings and described in the specification are intended to be encompassed by the invention.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

What is claimed is:

1. A method and preparation for the delivery of a selective small molecule P and P active media through a cell membrane comprising the preparation of a foodstuff such that: a) the foodstuff contains one or more nutrients; b) the one or more nutrients selected from the foodstuff receive a selective small molecule P and P active media; c) the one or more selective small molecule P and P active media attaches to a nutrient selected from the foodstuff; such that, d) the prepared foodstuff is consumable;

wherein by attaching the selective small molecule P and P active media to the nutrient selected from the foodstuff is meant that a chemical bond is formed between the selective small molecule P and P active media and the selected nutrient;

wherein by chemical bond is meant a combination of the selective small molecule P and P active media and the selected nutrient into a single chemical compound;

wherein the method and preparation for the delivery of a selective small molecule P and P active media through a cell membrane is configured for use in delivering a selective small molecule P and P active media through a cell membrane;

wherein the selective small molecule P and P active media is a Phytochemical substance that has a physical effect selected from the group consisting of: a) a biochemical effect on a biological organism; and, b) a Pharmacological effect on a biological organism;

wherein by small molecule is meant that the selective small molecule P and P active media has a molecular weight of less than 1000 Daltons;

wherein the combination of the foodstuff and the selective small molecule P and P active media are selected such that when the selected nutrient is brought through the cell membrane as part of the cellular metabolic process, the selective small molecule P and P active media is brought through the cell membrane with the selected nutrient;

wherein the chemical bond attaching the selected nutrient and the selective small molecule P and P active media is broken using enzymatic reactions once the combination of the foodstuff and the selective small molecule P and P active media have passed through the cell membrane;

wherein the selected nutrient is a chemical compound that forms an energy source that supports the metabolic activity of the cell;

wherein the selected nutrient is derived from the foodstuff;

wherein the chemical bond is formed using one or more chemical reactions selected from the group consisting of: a) a halogenation reaction; b) a hydrogenation reaction; c) a condensation reaction; and, d) a dehydration reaction;

wherein the selected nutrient is a carbohydrate;

wherein the selective small molecule P and P active media is lycopene.

* * * * *